United States Patent
Yanagisawa

(10) Patent No.: US 7,368,588 B2
(45) Date of Patent: *May 6, 2008

(54) PREPARATION OF SULFIDE CHAIN-BEARING ORGANOSILICON COMPOUNDS

(75) Inventor: Hideyoshi Yanagisawa, Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/273,084

(22) Filed: Nov. 15, 2005

(65) Prior Publication Data

US 2006/0106241 A1     May 18, 2006

(30) Foreign Application Priority Data

Nov. 16, 2004   (JP)   ............................. 2004-331389

(51) Int. Cl.
*C07F 7/04*     (2006.01)

(52) U.S. Cl. ..................................... 556/427

(58) Field of Classification Search ................. 556/427
See application file for complete search history.

(56) References Cited

U.S. PATENT DOCUMENTS

| | | |
|---|---|---|
| 5,405,985 A | 4/1995 | Parker et al. |
| 5,468,893 A | 11/1995 | Parker et al. |
| 5,483,245 A | 1/1996 | Ruinet |
| 5,663,395 A | 9/1997 | Gobel et al. |
| 6,015,870 A | 1/2000 | Ichinohe et al. |
| 6,294,683 B1 | 9/2001 | Johnson et al. |
| 6,448,426 B1 | 9/2002 | Backer et al. |
| 2003/0176719 A1 | 9/2003 | Yanagisawa et al. |

FOREIGN PATENT DOCUMENTS

| | | |
|---|---|---|
| EP | 1 342 750 A1 | 9/2003 |
| JP | 9-169774 A | 6/1997 |
| JP | 11-100388 A | 4/1999 |
| JP | 2003-261580 A | 9/2003 |
| JP | 2004-521945 A | 7/2004 |
| JP | 2004-521946 A | 7/2004 |
| WO | WO-03/002576 A1 | 1/2003 |
| WO | WO-03/002578 A1 | 1/2003 |

*Primary Examiner*—Samuel A Barts
(74) *Attorney, Agent, or Firm*—Birch, Stewart, Kolasch & Birch, LLP

(57) ABSTRACT

By reacting a mixture of a halogenoalkyl group-bearing organosilicon compound and sulfur with an aqueous solution or water dispersion of an ammonium or alkali metal sulfide or a hydrate thereof in the presence of a phase transfer catalyst, a sulfide chain-bearing organosilicon compound having the average compositional formula (2):

$$(R^1O)_{(3-p)}(R^2)_p Si-R^3-S_m-R^3-Si(OR^1)_{(3-p)}(R^2)_p \qquad (2)$$

wherein m has an average value of $2 \leq m \leq 6$ is obtained in high yields and at a low cost with minimized formation of a monosulfide-bearing organosilicon compound.

6 Claims, No Drawings

PREPARATION OF SULFIDE CHAIN-BEARING ORGANOSILICON COMPOUNDS

CROSS-REFERENCE TO RELATED APPLICATION

This non-provisional application claims priority under 35 U.S.C. §119(a) on Patent Application No. 2004-331389 filed in Japan on Nov. 16, 2004, the entire contents of which are hereby incorporated by reference.

FIELD OF THE INVENTION

This invention relates to a method for preparing a sulfide chain-bearing organosilicon compound having the average compositional formula (2):

$$(R^1O)_{(3-p)}(R^2)_p Si-R^3-S_m-R^3-Si(OR^1)_{(3-p)}(R^2)_p \qquad (2)$$

wherein $R^1$ and $R^2$ each are a monovalent hydrocarbon group of 1 to 4 carbon atoms, $R^3$ is a divalent hydrocarbon group of 1 to 10 carbon atoms, m has an average value of 2 to 6, and p is 0, 1 or 2, using a phase transfer catalyst while minimizing formation of a monosulfide-bearing organosilicon compound.

BACKGROUND OF THE INVENTION

In silica-loaded tires, bis-triethoxysilyltetrasulfide is widely used as a coupling agent between rubber and silica. However, when mixed with rubber and silica at elevated temperatures, this compound acts to increase the viscosity of the blend, which is inconvenient to subsequent operation.

To overcome this problem, shorter chain polysulfide compounds such as bis-triethoxysilylpropyldisulfide were proposed. For example, JP-A 9-169774 discloses a method for preparing disulfide silanes using NaCN. This method, however, has the problem of using the toxic compound. It would be desirable to have a substitute safe method of preparing short sulfide chain-bearing organosilicon compounds at low cost.

The inventors proposed in JP-A 11-100388 a method of preparing a short sulfide chain-bearing organosilicon compound by reacting a polysulfide silane of the general formula: $(RO)_3SiC_3H_6S_xC_3H_6Si(OR)_3$ wherein R is methyl or ethyl, and x is a positive number of 3 to 6 on the average, at least one anhydrous sulfur compound: $M^1{}_2S$ or $M^2S$ wherein $M^1$ is an alkali metal or ammonium and $M^2$ is an alkaline earth metal or zinc, and a halogenoalkoxysilane of the general formula: $XC_3H_6Si(OR)_3$ wherein X is halogen and R is methyl or ethyl. When the short sulfide chain-bearing organosilicon compound is prepared by this method, however, there can also be produced a monosulfide chain-bearing organosilicon compound, that is, an organosilicon compound having a sulfide chain which does not fully participate in the reactions with silica and rubber.

The inventors further proposed in JP-A 2003-261580 (US 2003-0176719 and EP 1342750A) a method for preparing a sulfide chain-bearing organosilicon compound, comprising the steps of:

premixing a sulfide chain-bearing organosilicon compound having the general formula (i):

$$(R^1O)_{(3-p)}(R^2)_p Si-R^3-S_m-R^3-Si(OR^1)_{(3-p)}(R^2)_p \qquad (i)$$

wherein $R^1$ and $R^2$ each are a monovalent hydrocarbon group of 1 to 4 carbon atoms, $R^3$ is a divalent hydrocarbon group of 1 to 10 carbon atoms, m has an average value of $2<m\leq 6$, and p is 0, 1 or 2, a halogenoalkyl group-bearing organosilicon compound having the general formula (ii):

$$(R^1O)_{(3-p)}(R^2)_p Si-R^3-X \qquad (ii)$$

wherein $R^1$ and $R^2$ each are a monovalent hydrocarbon group of 1 to 4 carbon atoms, $R^3$ is a divalent hydrocarbon group of 1 to 10 carbon atoms, X is a halogen atom, and p is 0, 1 or 2, and optionally, sulfur, adding anhydrous sodium sulfide represented by $Na_2S$ to the premix, and allowing reaction to take place for thereby forming a sulfide chain-bearing organosilicon compound having the general formula (iii):

$$(R^1O)_{(3-p)}(R^2)_p Si-R^3-S_n-R^3-Si(OR^1)_{(3-p)}(R^2)_p \qquad (iii)$$

wherein $R^1$ and $R^2$ each are a monovalent hydrocarbon group of 1 to 4 carbon atoms, $R^3$ is a divalent hydrocarbon group of 1 to 10 carbon atoms, n has an average value of $2\leq n<6$, satisfying m>n, and p is 0, 1 or 2, while minimizing formation of a monosulfide-bearing organosilicon compound with n=1.

This method, however, has some drawbacks. While substantially anhydrous sodium sulfide is used, it is time consuming to dry sodium sulfide hydrate. Filtration of the salt is necessary. A reaction medium is generally used and must be distilled off at the end of reaction. There still exists a need for a lower cost preparation method.

It is also known to prepare sulfide chain-bearing organosilicon compounds using phase transfer catalysts. This is taught in U.S. Pat. Nos. 5,405,985, 5,468,893, 5,483,245, 6,448,426, JP-A 2004-521945 and JP-A 2004-521946. Although these patents relate to methods for preparing sulfide chain-bearing organosilicon compounds using phase transfer catalysts, no reference is made to the control of formation of a monosulfide chain-bearing organosilicon compound.

SUMMARY OF THE INVENTION

An object of the present invention is to provide a safe and economical method for preparing a sulfide chain-bearing organosilicon compound of average compositional formula (2), shown below, having a minimal content of monosulfide chain-bearing organosilicon compound in its composition.

The inventors have discovered that when a mixture of a halogenoalkyl group-bearing organosilicon compound having the general formula (1):

$$(R^1O)_{(3-p)}(R^2)_p Si-R^3-X \qquad (1)$$

wherein $R^1$ and $R^2$ each are a monovalent hydrocarbon group of 1 to 4 carbon atoms, $R^3$ is a divalent hydrocarbon group of 1 to 10 carbon atoms, X is a halogen atom, and p is 0, 1 or 2, and sulfur is reacted with an aqueous solution or water dispersion of a sulfide having the formula $M_2S$ wherein M is ammonium or an alkali metal or a hydrate thereof in the presence of a phase transfer catalyst, a sulfide chain-bearing organosilicon compound having the average compositional formula (2):

$$(R^1O)_{(3-p)}(R^2)_p Si-R^3-S_m-R^3-Si(OR^1)_{(3-p)}(R^2)_p \qquad (2)$$

wherein $R^1$, $R^2$, $R^3$ and p are as defined above, and m has an average value of 2 to 6, can be prepared with minimized formation of a monosulfide-bearing organosilicon compound with m=1.

In an attempt to prepare a sulfide chain-bearing organosilicon compound having formula (2) using a phase transfer catalyst, if a sulfide $M_2S$ is reacted with sulfur and subsequently with a halogenoalkyl group-bearing organosilicon compound having formula (1), then a monosulfide-bearing organosilicon compound is formed in a more amount (e.g., equal to or more than 6 mol %). In contrast, if a halogenoalkyl group-bearing organosilicon compound having formula (1) is previously mixed with sulfur and subsequently reacted with an aqueous solution or water dispersion of a sulfide $M_2S$ or a hydrate thereof in the presence of a phase transfer catalyst, then the amount of a monosulfide-bearing organosilicon compound formed is significantly reduced (e.g., equal to or less than 3 mol %, and even equal to or less than 1.5 mol %). The present invention is predicated on this discovery that the order of reactions of reactants is significant in controlling formation of monosulfide-bearing organosilicon compound.

Accordingly the present invention provides a method for preparing a sulfide chain-bearing organosilicon compound having the average compositional formula (2), comprising the step of reacting a mixture of a halogenoalkyl group-bearing organosilicon compound having the general formula (1) and sulfur with an aqueous solution or water dispersion of a sulfide having the formula $M_2S$ or a hydrate thereof in the presence of a phase transfer catalyst to form the desired compound of formula (2) while minimizing formation of a monosulfide-bearing organosilicon compound with m=1.

The present invention is successful in reducing the content in the product of a monosulfide-bearing organosilicon compound of the average compositional formula (2) wherein m=1, especially to a level of 3 mol % or less. A sulfide chain-bearing organosilicon compound having the average compositional formula (2) wherein m has an average value of $2 \leq m \leq 6$, preferably $2 < m \leq 4$, and more preferably $2 < m < 3$, can be prepared in high yields.

In preparing a sulfide chain-bearing organosilicon compound from a halogenoalkyl group-bearing organosilicon compound using a phase transfer catalyst, the desired product is obtained in high yields and at low costs, and the product composition has a minimal content of a monosulfide-bearing organosilicon compound which is less reactive with rubber and wasteful. Therefore, the product is very useful in commercial application, for example, as an additive to silica-loaded tire rubber compositions.

DESCRIPTION OF THE PREFERRED EMBODIMENTS

Briefly stated, according to the present invention, by reacting a mixture of a halogenoalkyl group-bearing organosilicon compound having the general formula (1):

and sulfur with a solution or dispersion in water of a sulfide having the formula $M_2S$ or a hydrate thereof in the presence of a phase transfer catalyst, a sulfide chain-bearing organosilicon compound having the average compositional formula (2):

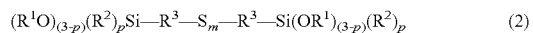

is obtained while minimizing formation of a monosulfide-bearing organosilicon compound of formula (2) wherein m=1.

One starting reactant is a halogenoalkyl group-bearing organosilicon compound having the following general formula (1).

In the formula, $R^1$ and $R^2$ are independently selected from monovalent hydrocarbon groups having 1 to 4 carbon atoms, for example, alkyl and alkenyl groups such as methyl, ethyl, n-propyl, i-propyl, n-butyl, i-butyl, t-butyl, allyl and methallyl, with methyl and ethyl being preferred. $R^3$ is selected from divalent hydrocarbon groups having 1 to 10 carbon atoms, for example, alkylene, arylene and alkenylene groups and combinations thereof, such as methylene, ethylene, propylene, n-butylene, i-butylene, hexylene, decylene, phenylene, and methylphenylethylene, and combinations thereof. Of these, ethylene and propylene are preferred, with propylene being most preferred. X is a halogen atom such as chlorine, typically Cl, Br or I, and preferably Cl or Br. The subscript p is equal to 0, 1 or 2, preferably 0 or 1, and most preferably 0.

Typical examples of the compound of formula (1) are given below.

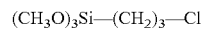

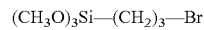

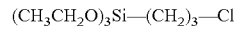

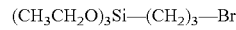

The phase transfer catalyst used herein is selected from quaternary onium cations, for example, tetrabutylammonium bromide, tetrabutylammonium chloride, tetramethylammonium bromide, tetramethylammonium chloride, tetraethylammonium bromide, tetraethylammonium chloride, tetrabutylammonium phosphate, tetrabutylammonium phosphite, tetrabutylammonium sulfate, tetrabutylammonium fluoride, benzyltrimethylammonium bromide, and tetraphenylammonium bromide. Of these, tetra-n-butylammonium bromide and tetra-n-butylammonium chloride are preferred.

The phase transfer catalyst may be mixed either with a mixture of the compound of formula (1) and sulfur or with an aqueous solution or water dispersion of the sulfide $M_2S$ or hydrate thereof.

In the former case, the phase transfer catalyst may be mixed with a mixture of the compound of formula (1) and sulfur directly or after diluted with water. For dilution, the amount of water added may be 0 to about 500% by weight, preferably about 100 to about 300% by weight based on the weight of the phase transfer catalyst.

It is noted that the addition of water is optional. For example, water may also be added after the compound of formula (1) has been mixed with the phase transfer catalyst, with the amount of water added being the same as above.

If the phase transfer catalyst is added in a small amount or not added to a mixture of the compound of formula (1) and sulfur, the catalyst is added to an aqueous solution or water dispersion of the sulfide $M_2S$ or hydrate thereof.

Although the amount of the phase transfer catalyst added is not critical, it is generally 0.1 to 10.0% by weight, preferably 0.5 to 5.0% by weight, and more preferably 1.0 to 2.0% by weight, based on the weight of the compound of formula (1).

The sulfide has the formula $M_2S$ wherein M is ammonium or an alkali metal, for example, Na, K, Cs, Li or $NH_4$, and preferably Na. Examples of the sulfide $M_2S$ include $Na_2S$, $K_2S$, $Cs_2S$, $Li_2S$, and $(NH_4)_2S$, with $Na_2S$ being preferred. The sulfide may also take the form of a hydrate, for example, $Na_2S \cdot 6H_2O$ and $Na_2S \cdot 9H_2O$.

The sulfide is used in aqueous solution or water dispersion form. Although the amount of water added to the sulfide is not critical, water is preferably added in such amounts that a total amount of water is 1 to 200% by weight relative to the compound of formula (1). Outside the range, smaller amounts of water may allow the sulfide or hydrate thereof to precipitate, with the concomitant difficulty of dispersion, and larger amounts of water may facilitate the susceptibility of the compound of formula (1) to hydrolysis. More preferably, the total amount of water added is 30 to 100% by weight relative to the compound of formula (1).

With respect to the molar ratio of the compound of formula (1), the sulfide $M_2S$, and sulfur, it is a general practice to add the sulfide $M_2S$ and sulfur in accordance with the desired value of m in the average compositional formula (2) and use the compound of formula (1) in an equimolar amount to M of the sulfide $M_2S$. It is understood that the system becomes alkaline as the moles of the compound of formula (1) is reduced, and becomes nearly neutral as the moles of the compound of formula (1) is increased. Specifically, the molar ratio of the compound of formula (1) to the sulfide $M_2S$ is preferably from 1.9 to 2.2, more preferably from 2.0 to 2.1. The amount of sulfur added is determined so as to provide the desired value of m. The molar ratio of sulfur to the sulfide $M_2S$ is preferably from 1.0 to 5.0, more preferably from 1.0 to 3.0, most preferably from 1.0 to 2.0. In one specific example where 2 mol of the compound of formula (1) is reacted with 1 mol of the sulfide $M_2S$ and 3 mol of sulfur, the resulting compound has the average compositional formula (2) wherein m has an average value of 4. In another specific example where 2 mol of the compound of formula (1) is reacted with 1 mol of the sulfide $M_2S$ and 1 mol of sulfur, the resulting compound has the average compositional formula (2) wherein m has an average value of 2.

In preparing the compound of the invention, an organic solvent may or may not be used. While a solventless system is preferred, it is acceptable to use a solvent having low water solubility. For example, use may be made of aliphatic hydrocarbons such as pentane, hexane, heptane and octane and aromatic hydrocarbons such as benzene, toluene and xylene.

Although the reaction temperature is not critical, it is generally from room temperature to about 200° C., preferably about 40 to about 170° C., more preferably about 50 to about 100° C. The reaction time is generally 30 minutes or more, and the reaction proceeds to completion within about 1 hour to about 15 hours.

At the end of reaction, the reaction mixture is subjected to separatory operation so that it is separated into the desired compound layer and the water layer. If a salt has precipitated in the reaction mixture, water may be added to dissolve the salt, or filtration be made before and/or after the separation. Where a solvent is used, it may be distilled off in vacuum after the separation.

To remove water from the desired compound, water may be distilled off in vacuum after the separation. Alternatively, after the water layer is separated off, a desiccant is added to the desired compound for drying. Exemplary desiccants are sodium sulfate and magnesium sulfate.

The desired compound that is prepared by the inventive method has the average compositional formula (2).

$$(R^1O)_{(3-p)}(R^2)_p Si\text{—}R^3 S_m\text{—}R^3 Si(OR^1)_{(3-p)}(R^2)_p \qquad (2)$$

In the formula, $R^1$ and $R^2$ each are a monovalent hydrocarbon group having 1 to 4 carbon atoms, and $R^3$ is a divalent hydrocarbon group having 1 to 10 carbon atoms, examples of which are as illustrated in conjunction with formula (1). The subscript p is 0, 1 or 2. The subscript m has an average value of $2 \leq m \leq 6$, preferably $2 < m \leq 4$, and more preferably $2 < m < 3$. In the compound (mixture) obtained by the inventive method, the formation of the compound of formula (2) wherein m=1 is minimized to a level of at most 3 mol %, preferably at most 2 mol %, and especially at most 1 mol %.

Typical examples of the compound of formula (2) are given below wherein m has an average value as described above.

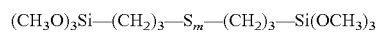

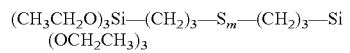

EXAMPLE

Examples of the invention are given below by way of illustration and not by way of limitation.

Example 1

A 1-liter separable flask equipped with a nitrogen gas inlet, thermometer, Dimroth condenser and dropping funnel was charged with 493.0 g (2.05 mol) of 3-chloropropyltriethoxysilane and 96.0 g (3.0 mol) of sulfur and heated at 80° C. To the flask was added an aqueous solution of 8.0 g of tetra-n-butylammonium bromide in 20 g of deionized water. Then an aqueous solution of 132.0 g (1.0 mol) of flake sodium sulfide having a sodium sulfide content of 59 wt % in 250 g of deionized water was slowly added dropwise so as to keep a temperature of 80-90° C. The time taken for dropwise addition was 40 minutes. After the completion of dropwise addition, the reaction mixture was held for 3 hours for ripening. Thereafter, the reaction mixture was cooled below 30° C. whereupon it separated into upper and lower layers. The lower layer was an aqueous solution in which NaCl formed was dissolved. The upper layer was 541.0 g. The upper layer was dried over 25 g of magnesium sulfate, followed by filtration. There was obtained 512.0 g of a brown clear liquid.

On analysis by infrared (IR) absorption spectroscopy and proton nuclear magnetic resonance ($^1$H-NMR) spectroscopy and sulfur content determination, it was confirmed to be a sulfide group-bearing alkoxysilane of the following average compositional formula.

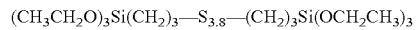

To confirm the sulfide distribution of the compound, supercritical chromatography was carried out. Its sulfide silane distribution (mol %) is shown below.

| | |
|---|---|
| m = 1 | ≦0.1% |
| m = 2 | 15.7% |
| m = 3 | 30.4% |
| m = 4 | 28.5% |
| m = 5 | 15.7% |
| m = 6 | 6.2% |

-continued

| | |
|---|---|
| m = 7 | 2.1% |
| m = 8 | 1.4% |

Example 2

A 1-liter separable flask equipped with a nitrogen gas inlet, thermometer, Dimroth condenser and dropping funnel was charged with 493.0 g (2.05 mol) of 3-chloropropyltri-ethoxy-silane and 41.6 g (1.3 mol) of sulfur and heated at 80° C. To the flask was added an aqueous solution of 8.0 g of tetra-n-butylammonium bromide in 20 g of deionized water. Then an aqueous solution of 132.0 g (1.0 mol) of flake sodium sulfide having a sodium sulfide content of 59 wt % in 250 g of deionized water was slowly added dropwise so as to keep a temperature of 80-90° C. The time taken for dropwise addition was 35 minutes. After the completion of dropwise addition, the reaction mixture was held for 5 hours for ripening. Thereafter, the reaction mixture was cooled below 30° C. whereupon it separated into upper and lower layers. The lower layer was an aqueous solution in which NaCl formed was dissolved. The upper layer was 470.0 g. The upper layer was dried over 25 g of magnesium sulfate, followed by filtration. There was obtained 445.0 g of a brown clear liquid.

On analysis by IR and $^1$H-NMR spectroscopy and sulfur content determination, it was confirmed to be a sulfide group-bearing alkoxysilane of the following average compositional formula.

$(CH_3CH_2O)_3Si(CH_2)_3-S_{2.3}-(CH_2)_3Si(OCH_2CH_3)_3$

To confirm the sulfide distribution of the compound, supercritical chromatography was carried out. Its sulfide silane distribution (mol %) is shown below.

| | |
|---|---|
| m = 1 | 0.9% |
| m = 2 | 70.7% |
| m = 3 | 25.1% |
| m = 4 | 2.7% |
| m = 5 | 0.6% |
| m = 6 | ≦0.1% |

Example 3

A 1-liter separable flask equipped with a nitrogen gas inlet, thermometer, Dimroth condenser and dropping funnel was charged with 493.0 g (2.05 mol) of 3-chloropropyltri-ethoxy-silane, 41.6 g (1.3 mol) of sulfur, and 5.0 g of tetra-n-butylammonium bromide and heated at 80° C. To the flask, an aqueous solution of 5.0 g of tetra-n-butylammonium bromide and 132.0 g (1.0 mol) of flake sodium sulfide having a sodium sulfide content of 59 wt % in 300 g of deionized water was slowly added dropwise so as to keep a temperature of 70-80° C. The time taken for dropwise addition was 50 minutes. After the completion of dropwise addition, the reaction mixture was held for 5 hours for ripening. Thereafter, the reaction mixture was cooled below 30° C. whereupon it separated into upper and lower layers. The lower layer was an aqueous solution in which NaCl formed was dissolved. The upper layer was 475.0 g. The upper layer was dried over 25 g of magnesium sulfate, followed by filtration. There was obtained 448.0 g of a pale brown clear liquid.

On analysis by IR and $^1$H-NMR spectroscopy and sulfur content determination, it was confirmed to be a sulfide group-bearing alkoxysilane of the following average compositional formula (same as in Example 2).

$(CH_3CH_2O)_3Si(CH_2)_3-S_{2.3}-(CH_2)_3Si(OCH_2CH_3)_3$

To confirm the sulfide distribution of the compound, supercritical chromatography was carried out. Its sulfide silane distribution (mol %) is shown below.

| | |
|---|---|
| m = 1 | 0.8% |
| m = 2 | 70.6% |
| m = 3 | 25.5% |
| m = 4 | 2.4% |
| m = 5 | 0.7% |
| m = 6 | ≦0.1% |

Example 4

A 1-liter separable flask equipped with a nitrogen gas inlet, thermometer, Dimroth condenser and dropping funnel was charged with 493.0 g (2.05 mol) of 3-chloropropyltri-ethoxy-silane, 48.0 g (1.5 mol) of sulfur, and 200.0 g of toluene and heated at 80° C. To the flask was added an aqueous solution of 8.0 g of tetra-n-butylammonium bromide in 20 g of deionized water. Then an aqueous solution of 132.0 g (1.0 mol) of flake sodium sulfide having a sodium sulfide content of 59 wt % in 300 g of deionized water was slowly added dropwise so as to keep a temperature of 90-95° C. The time taken for dropwise addition was 45 minutes. After the completion of dropwise addition, the reaction mixture was held for 5 hours for ripening. Thereafter, the reaction mixture was cooled below 30° C. whereupon it separated into upper and lower layers. The lower layer was an aqueous solution in which NaCl formed was dissolved. The upper layer was 690.0 g. The upper layer was dried over 25 g of magnesium sulfate, followed by filtration. There was obtained 665.0 g of a pale brown clear liquid. The liquid was concentrated in vacuum at 80° C., leaving 470.0 g of a pale brown clear liquid.

On analysis by IR and $^1$H-NMR spectroscopy and sulfur content determination, it was confirmed to be a sulfide group-bearing alkoxysilane of the following average compositional formula.

$(CH_3CH_2O)_3Si(CH_2)_3-S_{2.5}-(CH_2)_3Si(OCH_2CH_3)_3$

To confirm the sulfide distribution of the compound, supercritical chromatography was carried out. Its sulfide silane distribution (mol %) is shown below.

| | |
|---|---|
| m = 1 | 1.1% |
| m = 2 | 58.2% |
| m = 3 | 30.4% |
| m = 4 | 7.3% |
| m = 5 | 2.1% |
| m = 6 | 0.9% |
| m = 7 | ≦0.1% |

Comparative Example 1

A 1-liter separable flask equipped with a nitrogen gas inlet, thermometer, Dimroth condenser and dropping funnel was charged with 132.0 g (1.0 mol) of flake sodium sulfide having a sodium sulfide content of 59 wt %, 48.0 g (1.5 mol) of sulfur, 8.0 g of tetra-n-butylammonium bromide, and 300 g of deionized water, which were stirred for one hour at 80° C. Then 493.0 g (2.05 mol) of 3-chloropropyltriethoxysilane was slowly added dropwise so as to keep a temperature of 80-90° C. The time taken for dropwise addition was 40 minutes. After the completion of dropwise addition, the reaction mixture was held for 5 hours for ripening. Thereafter, the reaction mixture was cooled below 30° C. whereupon it separated into upper and lower layers. The lower layer was an aqueous solution in which NaCl formed was dissolved. The upper layer was 485.0 g. The upper layer was dried over 25 g of magnesium sulfate, followed by filtration. There was obtained 450.0 g of a pale brown clear liquid.

On analysis by IR and $^1$H-NMR spectroscopy and sulfur content determination, it was confirmed to be a sulfide group-bearing alkoxysilane of the following average compositional formula (same as in Example 4).

$(CH_3CH_2O)_3Si(CH_2)_3$—$S_{2.5}$—$(CH_2)_3Si(OCH_2CH_3)_3$

To confirm the sulfide distribution of the compound, supercritical chromatography was carried out. Its sulfide silane distribution (mol %) is shown below.

| | |
|---|---|
| m = 1 | 6.0% |
| m = 2 | 51.3% |
| m = 3 | 31.4% |
| m = 4 | 7.3% |
| m = 5 | 3.0% |
| m = 6 | 1.0% |
| m = 7 | ≦0.1% |

It is demonstrated that a more amount of monosulfide forms when reaction of sodium sulfide with sulfur is followed by reaction with 3-chloropropyltriethoxysilane.

Japanese Patent Application No. 2004-331389 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing a sulfide chain-bearing compound having the average compositional formula (2):

$(R^1O)_{(3-p)}(R^2)_pSi$—$R^3$—$S_m$—$R^3$—$Si(OR^1)_{(3-p)}(R^2)_p$ (2)

wherein $R^1$ and $R^2$ each are a monovalent hydrocarbon group of 1 to 4 carbon atoms, $R^3$ is a divalent hydrocarbon group of 1 to 10 carbon atoms, m has an average value of $2 \leq m \leq 6$, and p is 0, 1 or 2, the method comprising the sequential steps of first, reacting a mixture of a halogenoalkyl group-bearing organosilicon compound having the general formula (1):

$(R^1O)_{(3-p)}(R^2)_pSi$—$R^3$—$X$ (1)

wherein $R^1$ and $R^2$ each are a monovalent hydrocarbon group of 1 to 4 carbon atoms, $R^3$ is a divalent hydrocarbon group of 1 to 10 carbon atoms, X is a halogen atom, and p is 0, 1 or 2, and sulfur to form an intermediate reaction product, and then, reacting the intermediate reaction product with an aqueous solution or water dispersion of a sulfide having the formula $M_2S$ wherein M is ammonium or an alkali metal or a hydrate thereof in the presence of a phase transfer catalyst.

2. The method of claim 1 wherein the halogenoalkyl group-bearing organosilicon compound, sulfur and an aqueous solution or water dispersion of the phase transfer catalyst are mixed prior to the reaction with the aqueous solution or water dispersion of a sulfide having the formula $M_2S$ or a hydrate thereof.

3. The method of claim 1 wherein the sulfide chain-bearing organosilicon compound contains up to 3 mol % of a monosulfide-bearing organosilicon compound with m=1.

4. The method of claim 1 wherein in formula (2), m has an average value of 2<m<3.

5. A method for preparing a sulfide chain-bearing compound having the average compositional formula (2):

$(R^1O)_{(3-p)}(R^2)_pSi$—$R^3$—$S_m$—$R^3$—$Si(OR^1)_{(3-p)}(R^2)_p$ (2)

wherein $R^1$ and $R^2$ each are a monovalent hydrocarbon group of 1 to 4 carbon atoms, $R^3$ is a divalent hydrocarbon group of 1 to 10 carbon atoms, m has an average value of $2 \leq m \leq 6$, and p is 0, 1 or 2, said method comprising the steps of:

preparing a mixture of (i.) sulfur and (ii.) a halogenoalkyl group-bearing organosilicon compound having the general formula (1):

$(R^1O)_{(3-p)}(R^2)_pSi$—$R^3$—$X$ (1)

wherein $R^1$ and $R^2$ each are a monovalent hydrocarbon group of 1 to 4 carbon atoms, $R^3$ is a divalent hydrocarbon group of 1 to 10 carbon atoms, X is a halogen atom, and p is 0, 1 or 2; and subsequently reacting said mixture with an aqueous solution or water dispersion of a sulfide having the formula $M_2S$ wherein M is ammonium or an alkali metal or a hydrate thereof in the presence of a phase transfer catalyst.

6. The method of claim 5, for preparing a sulfide chain-bearing compound having the average compositional formula:

$(CH_3CH_2O)_3Si$—$(CH_2)_3$—$S_{3.8}$—$(CH_2)_3$—$Si(OCH_2CH_3)_3$ said method comprising the steps of:

preparing a mixture of (i.) sulfur and (ii.) 3-chloropropyltriethoxysilane; and reacting said mixture with an aqueous solution of sodium sulfide in the presence of tetra-n-butylammonium bromide.

* * * * *